United States Patent [19]

Updike et al.

[11] 4,421,853

[45] Dec. 20, 1983

[54] FERMENTATIVE PREPARATION OF L-LEUCINE

[75] Inventors: Mark H. Updike, Baltimore; Gary J. Calton, Elkridge, both of Md.

[73] Assignee: W. R. Grace & Co., New York, N.Y.

[21] Appl. No.: 388,760

[22] Filed: Jun. 16, 1982

[51] Int. Cl.$^3$ .................... C12P 13/06; C12N 15/00; C12R 1/13
[52] U.S. Cl. .................................. 435/116; 435/172; 435/840
[58] Field of Search ........................ 435/116, 172, 840

[56] References Cited

U.S. PATENT DOCUMENTS 3,865,690  2/1975  Okumura et al. ................... 435/116
3,970,519  7/1976  Tsuchida et al. ................... 435/116
4,237,228 12/1980  Zhdanova et al. .................. 435/116

*Primary Examiner*—Lionel M. Shapiro
*Attorney, Agent, or Firm*—Jill H. Krafte

[57] ABSTRACT

L-leucine is prepared by cultivation of an analogue-resistant mutant of *Brevibacterium thiogenitalis* in an aqueous nutrient medium under aerobic conditions. The cultivation is preferably carried out at about 30° C. and at a pH of 5 to 8. L-leucine is recovered from the fermentation broth.

6 Claims, No Drawings

FERMENTATIVE PREPARATION OF L-LEUCINE

BACKGROUND OF THE INVENTION

Production of L-leucine, L-valine and other amino acids via fermentation has been the subject of considerable research. Numerous genera of microorganisms have been employed along with various amino acid analogues. U.S. Pat. No. 3,865,690 teaches production of L-leucine by culturing a strain of Brevibacterium or Corynebacterium made resistant to a leucine antagonist. U.S. Pat. No. 3,970,519 cultures strains of the same genera in the presence of various amino acids to produce L-leucine. From U.S. Pat. No. 3,893,888 it is known that L-valine can be produced from mutant strains of Brevibacterium resistant to α-amino-β-hydroxy valeric acid (AHV). U.S. Pat. No. 3,688,073 teaches preparation of L-leucine using a microorganism of the genus Corynebacterium in the presence of a "promoter" for isoleucine, methionine, phenylalanine or valine, e.g. azaleucine or AHV. Azaleucine has been used as an analogue for producing L-leucine. See Wang et al, "Fermentation and Enzyme Technology," John Wiley and Sons, Inc., 1979, pages 18-20. U.S. Pat. No. 3,759,789 utilizes cultures of Arthrobacter alkanicus which are resistant to L-threonine. Precursors of L-leucine and L-isoleucine can be added to increase yields.

The following literature is relevant:

1. Araki, Kazumi, H. Ueda and S. Saigusa. Fermentative Production of L-Leucine with Auxotrophic Mutants of *Corynebacterium glutamicum. Agr. Biol. Chem.* 38(3), 565-572 (1974).
2. Calvo, R. A., and J. M. Calvo. Lack of End-Product Inhibition and Repression on Leucine Synthesis in a Strain of *Salmonella typhimurium. Science,* 156, 1107-1109 (1967).
3. Kisumi, M., S. Komatsubara and I. Chibata. Leucine Accumulations by Isoleucine Revertants of *Serratia marcescens* Resistant to α-Aminobutyric Acid: Lack of Both Feedback Inhibition and Repression, *J. Biochem.*, 73, 107-115 (1973).
4. Tsuchida, T., F. Yoshinaga K. Kubota, H. Momose and S. Okumura. Cultural Conditions for L-Leucine Production by Strain No. 218, a Mutant of *Brevibacterium lactofermentum* 2256. *Agr. Biol. Chem.* 39(5), 1149-1153 (1975).
5. Tsuchida, T., and H. Momose. Genetic Changes of Regulatory Mechanisms Occurred in Leucine and Valine Producing Mutants Derived from *Brevibacterium lactofermentum* 2256. *Agr. Biol. Chem.* 39(11), 2193-2198 (1975).
6. Tsuchida, T., F. Yoshinaga, K. Kubota, H. Momose and S. Okumura. Production of L-Leucine by a Mutant of *Brevibacterium lactofermentum* 2256. *Agr. Biol. Chem.* 38(10), 19097-1911 (1974).
7. Freundlich, M. and J. M. Trela. (1969). Control of isoleucine, valine, and leucine biosynthesis. *J. of Bacteriology*, 101-106.
8. Izumi, Y., Y. Asano, Y. Tani and K., Ogata. (1977). Formation of valine and leucine by analog-resistant mutants of an obligate methylotroph, *Methylomonas aminofaciens. J. Ferment. Technol.,* 55, 452-458.
9. Kisumi, M., S. Komatsubara and I. Chibata. (1977) Pathway for isoleucine formation from pyruvate by leucine biosynthetic enzymes in leucine-accumulating isoleucine revertants of *Serratia marcescens. J. Biochem.,* 82, 95-103.
10. Kisumi, M., J. Kato, S. Komatsubara, I. Chibata. (1973). Production of isoleucine, valine and leucine by regulatory mutants of *Serratia marcescens.* "Genetics of Industrial Microorganisms-Bacteria".
11. Rogerson, A., and M. Freundlich. (1969). Control of isoleucine, valine and leucine biosynthesis. VIII. Mechanism of growth inhibition by leucine in relaxed and stringent strains of *Escherichia coli* K-12. *Biochimica et Biophysica Acta,* BRA 26302.

Several general articles on biosynthetic pathways for producing L-leucine as well as other amino acids have also been published. See:

12. Szentirmai, A. and I Horvath. (1976). Regulation of branched-chain amino acid biosynthesis. *Acta Microbiol. Acad. Sci. Hung.,* 23, 137-149.
13. Umbarger, H. E. (1974). The elements involved in the multivalent regulation of the isoleucine and valine biosynthetic enzymes of the Enterobacteriaceae. *Proceedings of the 1st. Intersectional Congress of IAMS,* 1, Tokyo.
14. Umbarger, H. E. (1973). Genetic and physiological regulation of the isoleucine, valine and leucine biosynthetic enzymes of the Enterobacteriaceae. From "Genetics of Industrial Microorganisms."
15. Umbarger, H. E. (1978). Amino Acid Biosynthesis and Its Regulation. *Ann. Rev. Biochem.,* 47, 533-606, 563.

DESCRIPTION OF THE INVENTION

The invention is a process for preparing L-leucine which comprises cultivating under aerobic conditions a mutant strain of *Brevibacterium thiogenitalis* resistant to an analogue of L-leucine.

Wild strains of *Brevibacterium thiogenitalis* (e.g., ATCC 19240) selected for mutation are characterized by overproduction of glutamic acid. The biosynthetic pathway whereby microorganisms produce L-leucine is generally known. See for example Umbarger, "Amino Acid Biosynthesis and Its Regulation," *Ann. Rev. Biochem.* 1978. 47:563-565. As stated in this reference, the synthesis is believed to proceed through the following stages: pyruvate; α-acetolactate; α,β-dihydroxy isovalerate; α-ketoisovalerate; α-isopropylmalate; β-isopropylmalate; α-ketoisocaproate; L-leucine.

Certain analogues of the naturally occurring amino acids are suitable for isolating the mutant strains of this invention. These analogues are toxic to strains which do not overproduce L-leucine. Such analogues include α-amino-β-hydroxyvaleric acid; methallylglycine; and β-hydroxyleucine.

The leucine analogue resistant mutant may be obtained by ultraviolet irradiation of a wild type strain of *Brevibacterium thiogenitalis* or by treating the wild strain with a mutagen, e.g., ethyl methanesulfonate, N-methyl-$N_1$-nitro-N-nitrosoguanidine, etc. Thereafter the strain can be cultured in the presence of the analogue to isolate the colonies which overproduce L-leucine. For example the strain can be cultured at 30° C. for 2 to 7 days on agar plates of the following composition: gelatin hydrolysate peptone, 5.0 g/l; beef extractives, 3.0 g/l; agar, 15 g/l; α-amino-β-hydroxyvaleric acid sodium salt, 25 g/l.

A viable culture of an L-leucine-producing mutant strain of *Brevibacterium thiogenitalis* resistant to alphaamino-β-hydroxyvaleric acid (product of Example 2 below) has been deposited with the American Type Culture Collection, 12301 Park Lawn Dr., Rockville, Md. 20852, under No. ATCC 39104.

Fermentation of the isolated mutant strains of *Brevibacterium thiogenitalis* can be accomplished by shaking cultivation or submerged fermentation under aerobic conditions. The fermentation is carried out at 25° to 40° C. and at a pH of 5 to 8 (preferably 6.5 to 7.5). Calcium carbonate and ammonium may be employed for adjustment of the pH of the medium. The fermentation medium contains a source of carbon, a source of nitrogen and other elements. Suitable sources of carbon for the fermentation include fermentable sugars, protein hydrolysates and proteins. Examples of suitable sources of nitrogen are urea, ammonium salts of organic acids (e.g., ammonium acetate and ammonium oxalate) and ammonium salts of inorganic acids (e.g., ammonium sulfate, ammonium nitrate or ammonium chloride). The amounts of the carbon and nitrogen sources in the medium are from 0.001 to 20 w/v percent. Also, organic nutrients (e.g., corn steep liquor, peptone, yeast extracts, soybean extracts) and/or inorganic elements (e.g., potassium phosphate, magnesium sulfate, vitamins such as biotin and thiamine, and amino acids, e.g., valine) may be added to the medium. The fermentation is accomplished in 16 to 176 hours, and L-leucine is accumulated in the fermentation broth.

After the fermentation is completed, i.e., from 0.1 to grams/liter of L-leucine is accumulated in the broth, cells and other solid culture components are removed from the fermentation broth by conventional procedures such as filtration or centrifugation. Known procedures may be employed in the recovery and/or purification of L-leucine from the filtrate or the supernatant solution. For instance, the filtered fermentation broth is treated with a strong cation exchange resin. Then the resin is eluted with a dilute alkaline solution such as aqueous ammonia. The eluates containing L-leucine are combined and concentrated. An alkanol such as methanol or ethanol is added to the concentrated solution. The precipitated crystals can be recrystallized from an aqueous alkanol such as aqueous methanol or aqueous ethanol to yield pure crystals of L-leucine.

The following examples illustrate without limiting the invention. "Difco" refers to *Difco Manual of Dehydrated Culture Media and Reagents for Microbiological and Clinical Laboratory Procedures*, Ninth Edition, Difco Laboratories Incorporated, Detroit, Mich. (1953).

EXAMPLE 1

A Nutrient Agar (Difco) slant of ATCC culture 19240, *Brevibacterium thiogenitalis*, grown for 2 days at 30° C., was washed with 0.1 M sodium phosphate buffer, pH 7.0. The resulting cell suspension was decanted into a sterile tube to which a mutagen, ethyl methanesulfonate (EMS) was added in sufficient quantity to provide a 0.08 M concentration. The EMS treated cells were then incubated for 18 hours at 30° C. to allow the mutagen to take effect.

After incubation, the cell suspension was centrifuged, the supernate was decanted, and the cells were resuspended in fresh buffer.

After two washings to remove any residual mutagen, the cells were plated out to a gradient plate of Nutrient Agar containing 25 g/l α-amino-β-hydroxy valeric acid (AHV) at the high end of the gradient.

Resistant mutants appearing at the high end of the plate were transferred to fresh Nutrient Agar plates. After incubation at 30° C. for 24 hours, the isolates were inoculated into 1 ml tubes of Isoleucine Medium 1.

| Isoleucine Medium 1 | |
| --- | --- |
| | per liter DI[1] $H_2O$ |
| Glucose | 100 g |
| $KH_2PO_4$ | 3 g |
| $MgSO_4.7H_2O$ | 0.4 g |
| $FeSO_4.7H_2O$ | 0.01 g |
| $MnSO_4.H_2O$ | 0.0075 g |
| $(NH_4)_2SO_4$ | 50 g |
| Biotin | 100 μg |
| Thiamine HCl | 1 mg |
| Bacto-soytone[2] (Difco) | 0.63 g |
| $CaCO_3$ | 50 g |

[1]DI = deionized
[2]An enzymatic hydrolysate of soybean meal. "Difco," p. 264.

The pH was adjusted to 7.2 with NaOH prior to autoclaving @112° C. for 15 minutes.

The tubes were incubated for 4 days at 30° C., 300 RPM. A bioassay using *Pediococcus cerevisiae* (ATCC 8042) was performed as described below to determine the amount of L-leucine present. A resistant isolate designated 19240-31 was assayed at 2.6 g/l L-leucine.

Principle

*Pediococcus cerevisiae* requires all the amino acids, in their L forms, for growth. It is possible, therefore, to determine the amount of a particular amino acid present in a fermentation broth by spreading a lawn of Pediococcus on an agar medium containing all the necessary nutrients except the amino acid to be assayed. When a sterile filter disc, imbued with a Millipore-filtered fermentation broth is placed on the surface of the medium, the zone of Pediococcus growth around the disc may be measured and compared with a standard curve. The curve is prepared by growing the Pediococcus in the presence of filter discs containing known amounts of the amino acid to be assayed.

Procedure (for leucine assay)

*Pediococcus cerevisiae* ATCC 8042 is grown for ca. 44 hours at 37° C. in 4×10 ml of Micro Inoculum Broth (Difco). The cells are washed three times with sterile D.I. $H_2O$ then combined and resuspended in 12 ml sterile D.I. $H_2O$. Plates of Leucine Assay Medium (Difco) prepared by admixing 2.6 gm Leucine Assay Medium and 1.5 gm Agar Noble with 100 ml D.I. $H_2O$, are spread with a lawn of the cell suspension (0.3 ml). (Note: Micro Inoculum Broth is a commercially available culture medium containing peptone, yeast extract, dextrose, $KH_2PO_4$, and sorbitan monoleate complex. It is described on p. 213, "Difco." Leucine Assay Medium is likewise commercially available and is described on pp. 230–231, "Difco.")

After the excess moisture is allowed to evaporate from the plates, ¼" sterile absorbent discs (commercially available) are imbued with known amounts of L-leucine for construction of a standard curve, and with filtered fermentation broths to be assayed.

The plates are incubated for 24 hours at 37° C. after which time the diameter of the zones of growth are measured and recorded in millimeters. A standard curve is prepared against which the unknowns may be compared for determination of L-leucine production.

This procedure, due to its reliance on a microbiological indicator, provides a qualitative rather than a strictly quantitative measurement of amino acid production.

EXAMPLE 2

It was discovered that isolate 19240-31 was a mixed population of large and small colonies on Nutrient Agar. When grown in Isoleucine Medium #1 for 3 days at 30° C., 300 RPM, it was determined that the large colonies produced more valine than leucine and isoleucine, while the reverse was true of the small colonies. A bioassay was performed using *Pediococcus cerevisiae*. An isolate designated 19240-31-I produced 0.5 g/l leucine. An isolate designated 19240-31-K produced 1.5 g/l leucine and was subsequently deposited with ATCC and given the accession number ATCC 39104.

EXAMPLE 3

To determine the effect of initial pH of the growth media as well as that of flask size and incubation time, Isoleucine Medium 1 was prepared, and various aliquots of the medium were adjusted with NaOH to a range of pH levels (i.e.: 5.8 to 8.2 before autoclaving).

Isolate 19240-31-K was grown for various lengths of time (i.e.: 3 to 5 days) in 500 ml non-indented Erlenmeyer flasks containing 100 ml medium and 250 ml indented and non-indented Erlenmeyer flasks containing 50 ml medium.

When grown for 4 days at 30° C., 300 RPM in a 250 ml indented Erlenmeyer flask containing media adjusted to pH 7.9 before autoclaving, isolate 19240-31-K had a titer of 3.2 g/l L-leucine as determined by the Pediococcus bioassay.

What is claimed is:

1. A process for preparing L-leucine which comprises cultivating under aerobic conditions a mutant strain of Brevibacterium thiogenitalis resistant to an analogue of L-leucine selected from the group consisting of α-amino-β-hydroxyvaleric acid; methallylglycine; and β-hydroxyleucine, to yield a fermentation broth, accumulating from about 0.1 to about 6 grams/liter L-leucine in said fermentation broth, and recovering the accumulated L-leucine from said fermentation broth.

2. A process as in claim 1 wherein the mutant is *Brevibacterium thiogenitalis* ATCC 39104.

3. A process as in claim 1 wherein the fermentation is carried out at a temperature of from 20° to 45° C. for from 16 to 176 hours.

4. A process as in claim 1 wherein the pH of the fermentation media during cultivation is from 5 to 8.

5. A process as in claim 1 wherein the mutant is *Brevibacterium thiogenitalis* ATCC 39104 and fermentation is carried out at from 25° to 40° C. for 16 to 176 hours at a pH of from 5 to 9.

6. A process as in claim 1 wherein the analogue is α-amino-β-hydroxy valeric acid.

* * * * *